US012721807B2

(12) United States Patent
Paufique

(10) Patent No.: US 12,721,807 B2
(45) Date of Patent: Sep. 1, 2026

(54) **USE OF A COSMETIC COMPOSITION FOR MATURE SKIN IN THE FORM OF A DRY AND SOLUBLE FILM COMPRISING AN EXTRACT OF *Tropaeolum majus* AND AN EXTRACT OF *Lens esculenta***

(71) Applicant: SOCIETE INDUSTRIELLE LIMOUSINE D'APPLICATION BIOLOGIQUE, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

(*) Notice: Subject to any disclaimer, the term of this patent is extended or adjusted under 35 U.S.C. 154(b) by 727 days.

(21) Appl. No.: 18/019,541

(22) PCT Filed: Aug. 3, 2021

(86) PCT No.: PCT/EP2021/071680
§ 371 (c)(1),
(2) Date: Feb. 3, 2023

(87) PCT Pub. No.: WO2022/029129
PCT Pub. Date: Feb. 10, 2022

(65) Prior Publication Data

US 2023/0285271 A1 Sep. 14, 2023

(30) Foreign Application Priority Data

Aug. 5, 2020 (FR) ...................................... 2008299

(51) Int. Cl.
*A61K 8/9789* (2017.01)
*A61K 8/02* (2006.01)
(Continued)

(52) U.S. Cl.
CPC .......... *A61K 8/9789* (2017.08); *A61K 8/0212* (2013.01); *A61Q 19/007* (2013.01); *A61Q 19/08* (2013.01)

(58) Field of Classification Search
None
See application file for complete search history.

(56) References Cited

U.S. PATENT DOCUMENTS 5,139,782 A * 8/1992 Jung .................... A61Q 19/008 514/844
2015/0342854 A1* 12/2015 Shibuya ............... A61K 8/9761 424/769
(Continued)

FOREIGN PATENT DOCUMENTS

CN 106580837 A 4/2017
CN 107929121 A 4/2018
(Continued)

OTHER PUBLICATIONS

English language translation of FR 3058057 A1, Publ. May 4, 2018. (Year: 2018).*

*Primary Examiner* — Dominic Lazaro
(74) *Attorney, Agent, or Firm* — Greer, Burns & Crain, Ltd.

(57) ABSTRACT

The present invention relates to the use of a cosmetic composition for treating mature skin, said cosmetic composition being in the form of a dry and soluble film and comprising at least two active ingredients derived from *Tropaeolum majus* and *Lens esculenta*.

6 Claims, 1 Drawing Sheet

(51) Int. Cl.

| | |
|---|---|
| ***A61Q 19/00*** | (2006.01) |
| ***A61Q 19/08*** | (2006.01) |

(56) References Cited

U.S. PATENT DOCUMENTS

| | | | | |
|---|---|---|---|---|
| 2016/0287493 | A1 * | 10/2016 | Agarwal | ................ A61K 8/731 |
| 2021/0022966 | A1 | 1/2021 | Paufique | |

FOREIGN PATENT DOCUMENTS

| | | | | |
|---|---|---|---|---|
| FR | 2945209 | A1 | 11/2010 | |
| FR | 2965483 | A1 | 4/2012 | |
| FR | 3058057 | A1 * | 5/2018 | ............... A61K 8/36 |
| FR | 3079145 | A1 | 9/2019 | |
| WO | WO 2016083141 | A1 | 6/2016 | |

* cited by examiner

USE OF A COSMETIC COMPOSITION FOR MATURE SKIN IN THE FORM OF A DRY AND SOLUBLE FILM COMPRISING AN EXTRACT OF *Tropaeolum majus* AND AN EXTRACT OF *Lens esculenta*

CROSS-REFERENCE TO RELATED APPLICATIONS

This application is a U.S. National Stage Application of PCT/EP2021/071680 filed Aug. 3, 2021, claiming the benefit of priority from French Patent Application FR2008299 filed Aug. 5, 2020, the entire disclosure of both applications is herein incorporated by reference.

TECHNICAL FIELD

The invention relates to the use of a cosmetic composition comprising at least one extract of *Tropaolum majus* and at least one extract of *Lens esculenta* intended to be applied to mature skin, said composition being in the form of a dry and soluble film.

PRIOR ART

Beyond the loss of firmness and the appearance of wrinkles, mature skin has its own characteristics. Indeed, with age, skin dehydration appears. Cell renewal weakens and microcirculation slows down. The complexion becomes dull and loses uniformity, and the skin is more prone to redness. The radiance of the complexion reflects the health of the skin; a dull complexion leads to a tired look and may accentuate the signs of aging.

Mature skin needs intense hydration, light and radiance. Nevertheless, because this skin is finer and more sensitive, it requires a gentle routine. The contribution of active ingredients dedicated to the hydration and radiance of the complexion, delivered to the skin in large quantities, is therefore a real cosmetic response adapted to the expectations of mature women.

This is the objective of the invention, which, to this end, proposes combining two particular plant extracts, one from *Tropaeolum majus* and the other from *Lens esculenta*, in a cosmetic composition in the form of a dry film, combining naturalness, biodegradability, sensoriality and a massive release of active agents for high anti-aging effectiveness. Indeed, the inventor has, surprisingly, identified and specifically combined two individually known active ingredients in a cosmetic composition in the form of a dry and soluble film.

There are already many cosmetic compositions containing plant extracts for anti-aging effectiveness. A cosmetic composition based on extracts of *Avena sativa, Lens esculenta* and *Tropaeolum majus* has in particular already been described (FR 3058057). This composition makes it possible to improve the overall appearance of the face owing to an increase in the radiance of the complexion, while having an effect on the microrelief and, in the long term, of the skin. However, this composition combines a mixture of three plant extracts.

Against all expectations, the inventor discovered that the specific combination of the active ingredients derived from *Tropaeolum majus* and *Lens esculenta* in the cosmetic composition in the form of a dry film made it possible to obtain an anti-aging effect and to improve the persistence of the effect. The cosmetic effect is thus prolonged, in particular the radiance of the complexion, the hydration, the healthy-glow effect and the anti-aging effect while applying less frequent treatment.

SUMMARY OF THE INVENTION

The invention thus proposes another solution, namely a cosmetic composition in the form of a dry and soluble film and its cosmetic use on mature skin. Indeed, the compositions with the highest concentrations of active ingredients on the cosmetics market are masks. They generally contain a greater quantity of active ingredients than skincare formulations with an application time of the order of 10 to 30 minutes. These in particular include hydrogel masks or sheet masks, inspired by Asian beauty rituals, which contain an ultra-fine material impregnated with a lotion. Even though some of these masks claim a significant quantity of active agents in their composition, the bioavailability of the active ingredients in the skin is not satisfactory.

There are also dressings or adhesive patches containing a soluble film, which may itself contain active compounds. This film comes in a dry dosage form and may be used for cosmetic or therapeutic purposes (FR 3029103). However, such a film does not describe either a particular cosmetic application or a combination of particular active agents and does not make it possible to meet the objective of the invention.

Solely cosmetic applications of such a film containing a cosmetic active ingredient are also known, making it possible in particular to promote the penetration of said active ingredient into the skin in large quantities and/or more rapidly, and consequently to improve the cutaneous bioavailability of said active ingredient (FR 3079145). The application of said film does not describe a combination of particular active agents and does not describe any particular cosmetic application, and therefore no action on mature skin.

Thus, the subject of the invention is a cosmetic composition in the form of a dry and soluble film comprising at least one active ingredient derived from *Tropaeolum majus* and at least one active ingredient derived from *Lens esculenta* and/or its cosmetic use on mature skin. Preferably, said composition contains two active ingredients, namely an active ingredient derived from *Tropaeolum majus* and an active ingredient derived from *Lens esculenta*, and optionally a cosmetically acceptable excipient and/or the cosmetic use thereof on mature skin.

Such a composition preferably comprises between 0.2% and 1.5% of at least one active ingredient derived from *Tropaeolum majus* (by weight of the composition) and between 0.5% and 1.5% of at least one active ingredient derived from *Lens esculenta* (by weight of the composition).

Preferably, the composition also comprises, in addition to the active ingredients:

i. at least one mineral filler, and ii. at least two polymers of natural origin, and iii. at least one plasticizer, and iv. at least one surfactant.

Finally, the invention relates to a cosmetic use, in particular in the form of a cosmetic topical treatment for mature skin, in order to moisturize the skin and/or to improve the radiance of the complexion and/or for an anti-aging effect. Preferably, the skin is moistened beforehand prior to depositing the cosmetic composition in the form of a film.

Other features and advantages will become apparent from the detailed description and the figures of the invention that follow.

FIGURES

DETAILED DESCRIPTION OF THE INVENTION

Definitions

Figure 1:
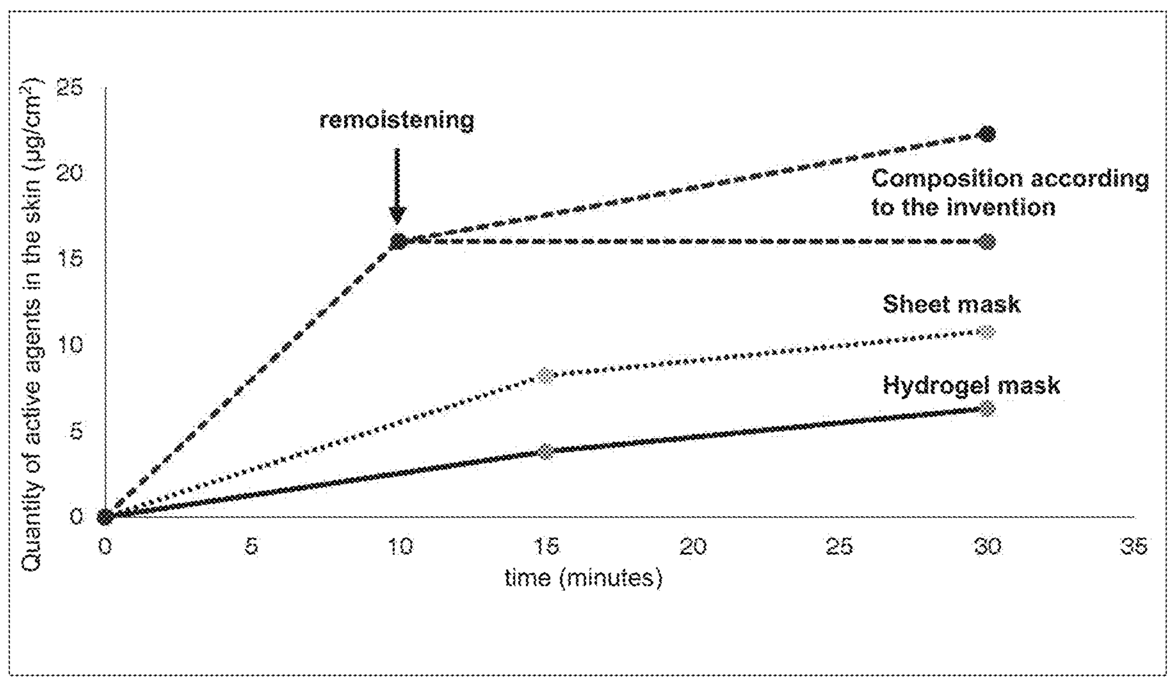
FIG. 1 shows a comparison of the quantity of active agents in the skin after application of a composition according to the invention, of a hydrogel mask and of a sheet mask.

"Film," within the meaning of the invention, is understood to mean a cosmetic product that is applied momentarily to the skin and removed after a certain application time, and that exhibits a cosmetic or dermocosmetic effect. It may be a face mask, for example.

"Dry film," within the meaning of the invention, is understood to mean a film having a water activity of less than 0.6.

"Mature skin" is understood to mean healthy skin, affected by normal skin aging. In particular, "healthy skin," within the meaning of the invention, is understood to mean the skin of a human subject. Thus, the use of the cosmetic composition intended to be applied to mature skin is not aimed at any therapeutic claim.

Within the meaning of the present invention, "extract" of a raw material X means any molecule or mixture of at least two molecules obtained from a raw material X, regardless of the method of extraction of said molecule or molecules. It may for example be an extract obtained by aqueous and/or hydroalcoholic and/or hydroglycolic extraction and/or obtained after a hydrolysis step.

"Cosmetic active ingredient" or "cosmetic active agent" or "active ingredient" or "active agent," within the meaning of the invention, are understood to mean one or more molecules, preferably a set of molecules, having a cosmetic effect when applied to the skin.

"Active ingredient derived from X" is also understood to mean an extract of X, in particular any molecule or mixture of molecules derived from X, obtained by any method. It may for example be an extract obtained by aqueous extraction or else by chemical or enzymatic hydrolysis.

"Polymer of natural origin" or "biopolymer," within the meaning of the invention, are understood to mean polymers derived from natural raw materials, as opposed to synthetic polymers that are obtained by chemical synthesis.

"Water content" of the dry film is understood to mean the quantity of liquid water contained in the film (weight ratio of water to the total weight of the film).

Cosmetic Composition

The invention thus relates to a cosmetic composition in the form of a dry and soluble film comprising at least one active ingredient derived from *Tropaeolum majus* and at least one active ingredient derived from *Lens esculenta.*

The film preferably has a water activity of less than 0.6. This parameter, well known to a person skilled in the art, makes it possible to identify the availability of water in the material. It can be measured by means of a device known as an AW meter, such as a LabSwift-AWAW meter. The value is unitless and between 0 and 1.

The water content of the dry and soluble film of which the cosmetic use is the subject of the invention is preferably less than 6 wt. % of the total weight of the dry film. This parameter is different from the water activity and is measured by successive weighings before and after drying in an oven.

The solubility of the dry film of which the cosmetic use is the subject of the invention is preferably determined as follows: a round of film having a diameter of 3.5 cm is placed in 20 mL of water at 25° C. while stirring at 200 rpm. A film is considered to be soluble within the meaning of the invention when it is completely dissolved in less than an hour.

Film thickness is measured using a micrometer. Since the thickness of the film is not constant over its entire length, this measurement must be carried out in several places in order to calculate an average. Preferably, the target average thickness of the film is between 75 and 95 μm.

In order to obtain a repeatable measurement to define standards, it is also possible to use the notion of basis weight. Thus, the film according to the invention has a target basis weight of between 100 and 120 $g/m^2$ The composition according to the invention comprises at least one active ingredient derived from *Tropaeolum majus* and at least one active ingredient derived from *Lens esculenta*. Preferably, the composition according to the invention consists of the combination of an active ingredient derived from *Tropaeolum majus* and an active ingredient derived from *Lens esculenta*, and optionally at least one cosmetically acceptable excipient.

An active ingredient derived from *Tropaeolum majus* has already been described for improving the oxygenation of the skin tissue and thus giving a healthy-glow effect (FR 2965483). An active ingredient derived from *Lens esculenta* seed has also been described for tightening pores, refining the texture of the skin, reducing the surface area of the pores and reducing shine (FR 2945209). However, the combination within the meaning of the invention has never been described.

Lentil, *Lens esculenta* or its synonym *Lens culinaris*, is an annual herbaceous plant of the Faboideae family. The lentil is mainly used in food. According to pharmacology, lentils are soothing, astringent, diuretic, laxative, tonic, hepatoprotective and stimulate the appetite. In Ayurveda, the seeds are mixed with butter to combat diarrhea and malabsorption syndrome, and lentil flour mixed with honey and pomegranate juice is used against vomiting. Also, the fried grains are mixed with honey and milk and applied to the skin to treat skin spots.

Nasturtium, *Tropaeolum majus*, is an annual herbaceous plant belonging to the Tropaeolaceae family. It is also used in food; in particular, nasturtium leaves and flowers are added raw to salads, sauces and mayonnaise. Nasturtium is rich in vitamin C and has antiseptic, stimulating, expectorant and diuretic properties.

Preferably, the active ingredient from *Tropaeolum majus* represents between 0.2% and 1.5% by weight of the composition (that is to say, of the film) and the active ingredient from *Lens esculenta* represents between 0.5% and 1.5% by weight of the composition.

Unless otherwise indicated, all the percentages "by weight of the composition" are given by weight relative to the total weight of the dry matter of the cosmetic composition (that is to say, of the film). The weight of dry matter can be obtained by drying the film at 80° C. until complete evaporation of the residual water and obtaining a constant weight under conditions that do not degrade the constituents of the film.

The cosmetic composition according to the invention preferably comprises an extract of *Tropaeolum majus* comprising arabinogalactans and a quantity of phenolic compounds of less than 0.2%. According to one embodiment, the arabinogalactans derived from the *Tropaeolum majus* extract have a degree of polymerization varying from 2 to 6.

The active ingredient derived from *Tropaeolum majus* may be obtained by any suitable method, in particular by aqueous extraction.

The *Lens esculenta* extract preferably comprises oligosaccharides. Preferably, the extract also has a carbohydrate content greater than 16% relative to the total dry matter content. Even more preferentially, at least 70% by mass of the carbohydrates present in the *Lens esculenta* extract are in the form of oligosaccharides, preferentially in the form of trehalose, maltose, maltotriose, stachyose and/or verbascose.

The active ingredient derived from *Lens esculenta* may be obtained by any suitable method, in particular by hydrolysis, in particular enzymatic hydrolysis of an aqueous extract.

The cosmetic composition also comprises, in addition to the two cosmetic active ingredients, constituents that are compatible and/or necessary for topical cosmetic application in the form of a dry and soluble film. Such constituents are mineral fillers, polymers of natural origin, plasticizers and surfactants.

Thus, the composition preferably further comprises:

i. at least one mineral filler, and ii. at least two polymers of natural origin, and iii. at least one plasticizer, and iv. at least one surfactant.

Preferably, the mineral filler is selected from kaolin, talc, sodium or calcium montmorillonite, mica, illite, perlite, diatom, potassium salts, sodium salts or calcium salts, and mixtures thereof. Even more preferably, the mineral filler is kaolin.

The composition comprises a mineral filler or a mixture of different mineral fillers, the content of mineral filler(s) representing between 5% and 25% by weight of the composition in film form.

The composition also comprises at least two polymers of natural origin. Preferably, the composition contains three polymers of natural origin. The polymer(s) of natural origin is/are selected from polymers extracted from plants or algae or microorganisms. Said polymer is preferably a polysaccharide of natural origin, selected from pullulan, cellulose, chitosan, acacia gum, guar gum, tara gum, gellan gum, konjac gum, xanthan gum, pectin, maltodextrin, cyclodextrins, polysaccharides, carrageenans, and mixtures thereof. The polymers of natural origin are preferably soluble in water.

The polymers can thus form a network making it possible in particular to maintain and concentrate the cosmetic active ingredients. Said composition thus comprises polymers of natural origin that represent at least 15% by weight of the composition, preferably between 15% and 75% by weight of said composition.

Particularly preferably, the polymers of natural origin are chosen from guar gum, carrageenans and cellulose.

The composition according to the invention also comprises at least one plasticizer that can be chosen from urea, urea derivatives (such as hydroxyethyl urea), glycerol, glycerol esters and ethers, monosaccharides, sorbitol, sucrose, amino acids, glycols such as butylene glycol or propylene glycol, fatty alcohols, salts, lactate esters and ethers and mixtures thereof.

Preferably, the plasticizer(s) represent(s) between 25% and 75% by weight of the composition. Preferably, the plasticizers are urea and/or glycerol.

Finally, the composition may comprise at least one surfactant chosen in particular from nonionic, anionic or cationic surfactants, preferably from nonionic surfactants. Mention will be made in particular of lecithins, sorbitan and fatty acid esters, and their derivatives, in particular those marketed under the names Span and Tween (polysorbates), in particular sorbitan monolaurate, or sorbitan monostearate. Said surfactant represents between 0.1% and 1.5% by weight of the composition. Preferably, said surfactant is sorbitan laurate.

Cosmetic Use

Advantageously, the composition according to the invention is composed of more than 75% of ingredients of natural origin and it is biodegradable. The combination of active ingredients derived from *Tropaeolum majus* and *Lens esculenta* in the form of a film according to the invention is a cosmetic response for mature skin making it possible to intensely moisturize as well as revive the radiance of the complexion. The active ingredients are delivered into the skin in large quantities and quickly. Preferably, the active ingredients diffuse into the skin 4.4 and 7.6 times faster than when they are delivered by a sheet mask or a hydrogel mask. In addition, compared to a sheet mask and a hydrogel mask, the composition according to the invention preferentially releases a quantity of active ingredients 1.5 and 2.5 times greater, respectively, whereas the sheet mask and the hydrogel mask are applied 3 times longer to the surface of the skin.

When the film is applied to the skin, especially facial skin, the specific active agents present in the film infuse mature skin. The skin is intensely and durably hydrated immediately, and the radiance of the complexion is revived for the day. In addition, prolonged use as a cure provides a firming and anti-wrinkle effect that lasts over time.

Advantageously, by inserting themselves within the polysaccharide matrix, the plasticizers and the mineral fillers facilitate the rehydration of the film and the adhesion of the film to the skin. The film and the skin are then in close contact and the exchange surface is maximized. A significant concentration gradient, comparable to a natural vectorization system for the active ingredients, then appears, thus optimizing the bioavailability of the active agents and their penetration into the heart of the skin.

This is why the invention is also specifically aimed at a cosmetic method for the non-therapeutic treatment of mature skin, that is to say, a cosmetic use, which consists in applying the composition according to the invention topically at least once on mature skin to improve the quality of mature skin.

Thus, a subject of the invention is also the use of a cosmetic composition for mature skin in the form of a dry and soluble film comprising at least one active ingredient derived from *Tropaeolum majus* and at least one active ingredient derived from *Lens esculenta.*

According to a preferred embodiment, the invention is aimed at a cosmetic use for a moisturizing effect on the skin and/or smoothing and/or improving the radiance of the complexion and/or anti-sebum and/or anti-wrinkle and/or anti-aging and associated with a residual effect. Preferably, the skin is moistened before application of the composition in order to have an optimal affinity with the skin.

Thus, the use corresponds to a cosmetic treatment that is an anti-aging treatment.

A particularly suitable application time is between 5 and 30 minutes, preferably between 10 and 30 minutes.

The film may be applied to the face for use, for example, as a mask in order to improve the radiance of the complexion, but also to any other part of the body. Preferably, the film is applied to mature skin, making it possible to moisturize the skin and improve the radiance of the complexion.

In order to obtain a cumulative effect, i.e. a cure effect, it is preferable to apply the film to the skin at least twice a week for 28 days.

The invention will now be illustrated by examples of cosmetic compositions in the form of films and test results demonstrating the cosmetic effectiveness of said compositions.

EXAMPLES

Preparation of Active Ingredients from *Tropaeolum majus* and *Lens esculenta*

A method for preparing an extract of *Tropaeolum majus* is described in particular in patent FR 2965483. The particularly suitable method comprises at least the following series of steps:

- solubilizing powder of aerial parts of *Tropaeolum majus* in water, preferably at a rate of at least 50 g/L,
- separating the soluble and insoluble phases,
- eliminating polyphenolic compounds by absorption, so as to obtain a content of phenolic compounds of less than 0.2% relative to the dry matter,
- filtering so as to recover an active ingredient containing arabinogalactans.

Steps of discoloration and deodorization of the soluble phase may be envisaged without modifying the active fraction of the active ingredients.

The parameters of the different steps must preferably be adjusted in order to obtain an active agent comprising arabinogalactans, in particular arabinogalactans having a degree of polymerization of between 2 and 6.

The dry matter content of the *Tropeolum majus* extract varies from 10 to 55 g/L, preferably from 22 to 35 g/L.

The pH may be between 3.0 and 7.0, preferably between 4.0 and 5.0. The total sugar content is preferably between 2 and 16 g/L, even more preferably between 5 and 10 g/L.

A non-limiting example of a *Tropaolum majus* active agent obtained has the following characteristics:

- appearance: clear, light yellow liquid with a characteristic odor
- dry matter content: 25.5 g/L
- pH: 4.5
- total sugar content (according to the DUBOIS method): 9.8 g/L or 38.4% by weight of dry matter A method for preparing a *Lens esculenta* active agent is described in patent FR 2945209. It comprises at least the following steps:

- aqueous solubilization of *Lens esculenta* seed powder
- enzymatic hydrolyses
- separating the soluble and insoluble phases,
- inactivating enzymes by heat treatment,
- filtering and concentrating the soluble phase to recover an active fraction comprising sugars, mainly oligosaccharides with a degree of polymerization of between 2 and 5,
- filtering and sterilizing filtration.

These steps are commonplace in the field of the extraction of active agents from plants, and a person skilled in the art is able to adjust the reaction parameters based on their general knowledge.

The dry matter content of the *Lens esculenta* active agent varies from 12 to 110 g/L, preferably from 42 to 62 g/L The pH may be between 3.0 and 7.0, preferably between 4.5 and 5.5. The total sugar content is preferentially between 3 and 35 g/L, preferentially between 10 and 20 g/L.

A non-limiting example of an obtained *Lens esculenta* active agent has the following characteristics:

- appearance: clear, light yellow liquid with a weak odor
- dry matter: 50.2 g/L
- pH: 5.0
- total sugar content (according to the DUBOIS method): 18.1 g/L or 36.1% by weight of dry matter
- protein content (according to the KJELDAHL method): 24.1 g/L or 48% by weight of dry matter

Preparation of a Cosmetic Composition According to the Invention

A method for preparing the composition according to the invention is described:

- formulation in liquid form of the various components: glycerol, kaolin, guar gum, urea, cellulose, carrageenan, *Tropaeolum majus* extract, *Lens esculenta* extract, Sorbitan laurate, potassium chloride, water.
- deposition of the formula on a support
- evaporation of water in an oven heated to a temperature between 70 and 100° C.
- laser cutting to desired shape

Example 1 of a Cosmetic Composition According to the Invention

An example of a composition according to the invention may be:

TABLE 1

| | % of the dry matter |
|---|---|
| Active ingredients from *Tropaeolum majus* and *Lens esculenta* | 1.8% |
| Mineral filler: kaolin | 14.2% |
| Natural polymers: Carrageenan, guar gum, cellulose | 32% |
| Plasticizers: urea, glycerol | 50.6% |
| Surfactant: sorbitan laurate | 1.4% |

The composition of Example 1 has the following characteristics shown in Table 2.

TABLE 2

| | |
|---|---|
| Dry matter content | 950 mg/g |
| Residual water (AW) | 0.3 |
| Mineral ash content | 140 mg/g |
| Total sugar content | 300 mg/g |
| Total nitrogen content | 400 mg/g |
| pH | 6.0 |
| Average thickness | 85 μm |
| Basis weight | 110 g/m$^2$ |

The dry matter content was determined by weighing the residues resulting from drying the samples of the composition at 80° C. in a moisture analyzer until a constant weight was obtained.

An aluminum dish is placed in the moisture analyzer and then tared. 2 g of sample is then distributed in the dish. The whole is heated to 80° C. until a constant weight is obtained. The dry matter content is displayed directly on the device.

The residual water corresponds to the activity of water (AW). To measure this, a sample of the composition is placed in the measurement chamber of the AW meter. The water activity value is displayed directly on the device.

The mineral ash content can be determined by weighing the residues from the incineration of the samples of the composition at 550° C. in an electric muffle furnace (VULCAN™ 3.550-NDI).

1 gram of sample is weighed into a previously tared crucible and is placed in the oven. The mineralization program comprises a first step of 3 hours at 110° C. followed by a second step of 9 hours at 550° C. The temperature of 550° C. is maintained until the ashes are white. The crucible and its contents are then immediately placed in a desiccator until they have completely cooled, after which they are weighed. The weight of the residue is calculated by deducting the tare.

The total sugars were assayed using the DUBOIS method (Dubois M. et al., *Analytical chemistry,* 28, 3, 350-356, 1956). All the reducing functions are released in the presence of concentrated sulfuric acid and, with phenol, give a yellow-orange colored compound. The coloration obtained, measured at 490 nm on a spectrophotometer, is proportional to the amount of total sugars in the sample. Calibration solutions were prepared from a glucose standard of 25 to 125 mg/L. A calibration curve of the optical densities of the calibration solutions as a function of their concentration was constructed.

The composition sample is dissolved beforehand at 50 g/L in water and 60° C., then diluted after cooling, with distilled water, so that the sugar content corresponds to the calibration range.

The amount of total sugars in the samples was determined using the calibration curve.

The total nitrogen was measured according to the KJELDHAL method (reference: Official method of analysis of the A.O.C., 12th ed. W Horwitz, E.D., New-York, 15-60, 1975).

The pH measurements were carried out directly on the film using a PH905 pH meter (Courage & Kazakha). The pH meter allows direct measurement of the pH of the film by applying a glass electrode to its surface.

The basis weight was measured as follows. In a room with controlled humidity and temperature (40% RH, 22° C.), discs of film 10 cm in diameter are cut and then weighed on a precision scale. The basis weight is expressed in g/m$^2$ by averaging the mass obtained for 3 film discs.

Example 2 of a Cosmetic Composition According to the Invention

Another example of a composition according to the invention may be:

TABLE 3

| | % of the dry matter |
|---|---|
| Active ingredients from *Tropaeolum majus* and *Lens esculenta* | 1.6% |
| Mineral filler: kaolin | 12.1% |
| Natural polymers: Carrageenan, guar gum, cellulose | 27.7% |
| Plasticizers: hydroxyethyl urea, glycerol | 57.4% |
| Surfactant: sorbitan laurate | 1.2% |

Examples of Masks According to the Prior Art

The formulas of these masks of the prior art were produced to implement comparative tests with the composition according to the invention. An example of a hydrogel mask may be

TABLE 4

| Ingredients | Composition (%) |
|---|---|
| Water | 76.6 |
| Aqueous extracts of *Tropaeolum majus* and *Lens esculenta* | 10 |
| Pentylene glycol | 3.0 |
| Preservative | 0.5 |
| Glycerin | 8.0 |
| Carrageenan | 0.8 |
| Carob gum | 0.6 |
| Sodium chloride | 0.5 |

An example of a sheet mask may be:

TABLE 5

| Ingredients | Composition (%) |
|---|---|
| Water | 78.2 |
| Aqueous extracts of *Tropaeolum majus* and *Lens esculenta* | 10 |
| Sodium gluconate | 0.1 |
| Sodium benzoate | 0.3 |
| Citric acid | 0.1 |
| 1,2-hexanediol | 1.0 |
| Glycerin | 3.0 |
| Glycereth-26 | 2.0 |
| Butylene glycol | 5.0 |
| Xanthan | 0.3 |

Results

Study of the Release of Active Ingredients

A study of the release of the active agents was carried out in order to define the quantity of the active ingredients of the composition according to the invention (as presented in the example) released on the skin. To do this, three cosmetic compositions in film form were produced: a film without active agent, a film containing the active ingredient of *Tropaeolum majus* and a film containing the active agent of *Lens esculenta*. For these experiments, the peptides of the *Lens esculenta* active agent were previously grafted with FITC (fluorescein isothiocyanate) and the carbohydrates of the *Tropaeolum majus* active agent were previously grafted with 5-DTAF (5-(4,6-dichlorotriazinyl) aminofluorescein).

The films were placed on the surface of the skin for a period of 10 minutes. The *Stratum corneum* is recovered using 15 successive strips and the fluorescence is quantified by spectrofluorimetry. The release of the active agents of the composition according to the invention is then evaluated by quantifying the fluorescence in the *Stratum corneum*. The results obtained are shown in table 5:

TABLE 6

| | 10 minutes | Flow |
|---|---|---|
| Quantity of the *Lens esculenta* active agent in the stratum corneum | 16.0 +/− 3.8 μg/cm² | 96 μg/cm²/h |
| Quantity of the *Tropaeolum majus* active agent in the stratum corneum | 8.9 +/− 2.2 μg/cm² | 53 μg/cm²/h |

The quantity of active agents delivered in 10 minutes by the composition according to the invention into the skin is very high, up to 16 μg/cm² of active agent. If we compare with face care containing 2.5% of active ingredient, a topical application according to the criteria of the SCCS (Scientific Committee on Consumer Safety) corresponds to 1.54 g of formula applied to a face of 565 cm², which brings only 3.4 μg/cm² of this active agent onto the surface of the skin, i.e. approximately 5 times less.

Comparative Tests of Bioavailability of Active Ingredients

Bioavailability studies were carried out in order to define the quantity of the active ingredients of the composition according to the invention (as presented in the example) released on the skin. To do this, the bioavailability of the composition according to the invention was evaluated in comparison with two other types of masks (a hydrogel mask described in Table 3 and a sheet mask having been soaked beforehand in the lotion described in Table 4). All the masks contain equivalent concentrations of active ingredients, that is to say, equivalent dry matter contents of the active agents. For these tests, the peptides from the *Lens esculenta* extract were previously grafted with FITC (fluorescein isothiocyanate).

The masks and the composition according to the invention were placed on the surface of the skin for a period of 30 minutes and various points of analysis were carried out at 10, 15 and 30 minutes. At these different times, the *Stratum corneum* is recovered using 15 successive strips (D'squames DS100) and the fluorescence is quantified by spectrofluorimetry.

The results presented in FIG. 1 show that after 10 minutes of application, the composition according to the invention releases 16 μg/cm² of the active agent from *Lens esculenta* in the *Stratum corneum.*

In comparison, after 30 minutes of application, the hydrogel mask and the sheet mask release only 6.3 μg/cm² and 10.8 μg/cm², respectively, of the active agent from *Lens esculenta.*

Thus, despite a longer application time for the sheet mask and the hydrogel mask, the quantities of active ingredients released in the *Stratum corneum* do not reach the values obtained with the composition according to the invention after only 10 minutes of application.

Moreover, according to FIG. 1, a second moistening of the film makes it possible to release 6 μg/cm² of active ingredients into the skin again. The rehydration of the film is therefore a step conditioning the release of the active ingredients.

Thus, compared to the sheet mask and the hydrogel mask, the composition according to the invention delivers a quantity of active ingredients 1.5 and 2.5 times greater, respectively.

Comparative Test of Delivery Speed of the Active Ingredients

Figure 2:
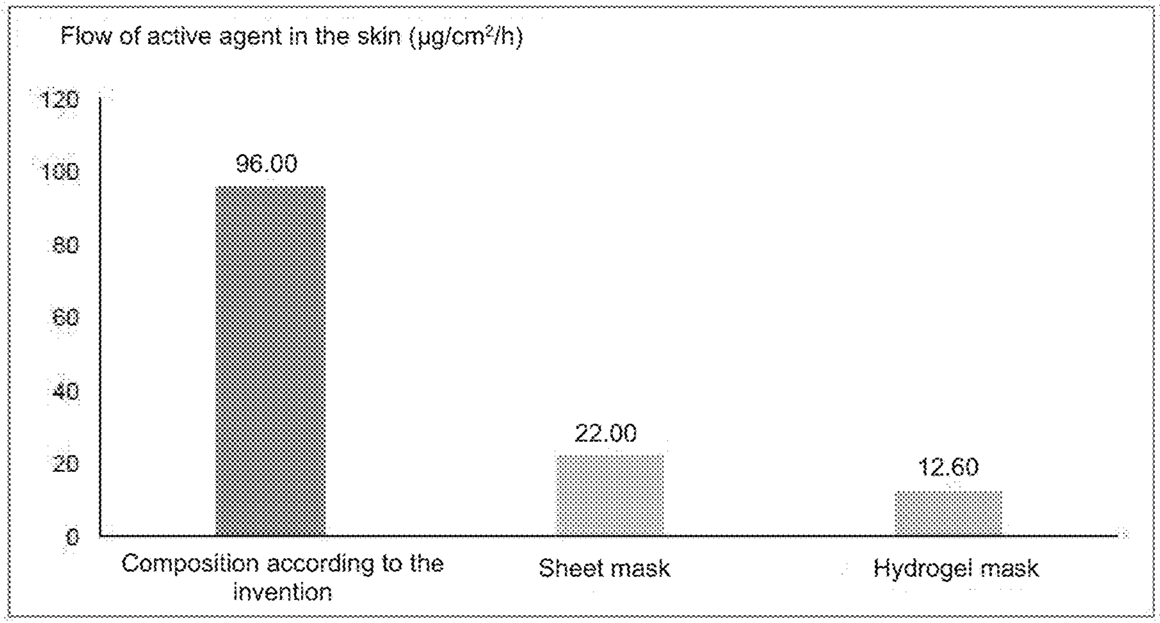
FIG. 2 shows the results of the bioavailability of the active agents of *Tropaeolum majus* and *Lens esculenta* formulated in the composition according to the invention compared with that of the combination formulated in a hydrogel mask or in a sheet mask.

The results presented in FIG. 2 demonstrate that the composition according to the invention delivers active ingredients of *Lens esculenta* and *Tropaeolum majus* with a flow of up to 96 μg/cm²/h, whereas the sheet mask and the hydrogel mask release them with flows of 22 μg/cm²/h and 12.6 μg/cm²/h, respectively.

Thus, compared to the sheet mask and the hydrogel mask, the composition according to the invention delivers the active ingredients of *Lens esculenta* and *Tropaeolum majus* into the *Stratum corneum* 4.4 and 7.6 times faster.

Short-Term Effect of the Composition According to the Invention

Study of the Immediate and Residual Effect Over the Day Following a Single Application The objective of this study is to evaluate, in vivo, the immediate effect of the cosmetic composition according to the invention on mature volunteers after 10 minutes of application as well as after a persistence period of 6 hours after application, corresponding to an effect on the day.

This study was carried out on 20 Caucasian, healthy, female volunteers, aged 72±4 years and presenting with a dull complexion and crow's feet wrinkles. In particular, the inventor studied the moisturizing effect by measuring the hydration rate using a Corneometer® CM 820 (Courage and Khazaka); the radiance of the complexion was evaluated by experts, and the smoothing effect by making silicone impressions then analysis by fringe projection.

Study Results

The composition according to the invention increases the hydration level of mature skin throughout the day. Indeed, immediately after application, a significant increase of 23% was observed, and this effect is visible for 90% of the volunteers. This hydration level is maintained throughout the day, with a significant increase maintained at 20% 6 hours after application. This effect is observed in 85% of volunteers.

The visual evaluation of the radiance of the complexion by experts demonstrates that the composition according to the invention makes it possible to observe a significant and immediate increase in the radiance of the skin by 21% in all volunteers. This effect is still 21% 6 hours after application. It also allows a significant and immediate improvement of the pink color, responsible for the fresh complexion, by 14%. This effect is maintained at 11% 6 hours after application, and there is a significant and immediate healthy-glow effect increased by 10%, observed in 75% of volunteers. This effect is still 10% 6 hours after application.

The composition according to the invention, immediately after application, significantly smooths the skin microrelief at the cheeks by 4% in 75% of volunteers. The composition according to the invention also allows an 11% reduction in the presence of wrinkles. This effect is maintained throughout the day with a 13% decrease in the presence of wrinkles 6 hours after application.

Thus, after a single 10-minute application, the composition according to the invention significantly improves the skin hydration of mature skin and the radiance of the complexion. This treatment also provides a smoothing effect. All these effects are maintained throughout the day.

Long-Term Effect of the Composition According to the Invention

During this study, the in vivo effect of the composition according to the invention was evaluated after a course of 12 applications of 10 minutes over a period of 28 days. This study was carried out on 19 healthy, female Caucasian volunteers aged 72±4 years. In particular, the inventor has studied the firming effect by measuring the biomechanical properties of the skin using a Cutometer® MPA 580 (Courage and Khazaka); the anti-wrinkle effect by studying the skin relief at the crow's feet by fringe projection; the skin texture by visual scoring evaluated by experts; the moisturizing effect by measuring the skin's hydration level using a Corneometer® CM 820 (Courage and Khazaka); the radiance of the complexion is evaluated by experts.

Study Results

Used as a cure, the composition according to the invention significantly improves the biomechanical properties of the skin. Thus, skin firmness is increased by 8%, effect observed in 89% of volunteers; elasticity is improved by 17%, effect observed in 79% of volunteers; skin tone is increased by 13%, effect observed in 84% of volunteers.

Used as a cure, the composition according to the invention significantly reduces crow's feet wrinkles. Thus, the surface roughness parameter Sa is reduced by 7%, which effect is observed in 89% of the volunteers; the volume of wrinkles is reduced by 16%, which effect is observed in 89% of the volunteers.

Used as a cure, the composition according to the invention significantly improves the skin texture in the cheeks. Indeed, experts highlight an 11% decrease in the level of pore dilation.

Used as a cure, the composition according to the invention significantly increases the hydration of the skin by 14%. This effect is observed in 79% of volunteers.

Used as a cure, the composition according to the invention significantly improves the radiance of the complexion with an increase in the radiance of the skin by 12%, observed in 89% of the volunteers; an 11% improvement in the pink color, responsible for the fresh complexion; a healthy-glow effect increased by 21%, observed in 95% of volunteers.

The invention claimed is:

1. A cosmetic composition for mature skin, wherein the cosmetic composition is in the form of a dry and soluble film, wherein the composition comprises:

at least one active ingredient derived from *Tropaeolum majus;* at least one active ingredient derived from *Lens esculenta,* at least one mineral filler, at least two polymers of natural origin, at least one plasticizer, and at least one surfactant.

2. The cosmetic composition of claim 1, wherein the active ingredient derived from *Tropaeolum majus* represents between 0.2% and 1.5% by weight of the composition and the active ingredient derived from *Lens esculenta* represents between 0.5% and 1.5% by weight of the composition.

3. The composition of claim 1, wherein the at least one mineral filler represents between 5% and 25% by weight of the composition;

the two or more polymers of natural origin represent between 15% and 75% by weight of the composition;

the at least one plasticizer represents between 25% and 75% by weight of the composition; and/or the at least one surfactant represents between 0.1% and 1.5% by weight of the composition.

4. The composition of claim 1, wherein the at least one mineral filler comprises kaolin, the plasticizers comprise urea and glycerol, the at least one surfactant comprises sorbitan laurate and the polymers of natural origin comprise guar gum polysaccharides, carrageenans and/or cellulose.

5. A method for a topical cosmetic treatment of mature skin, moisturizing the skin, and improving radiance of the skin complexion, the method comprising applying topically the composition of claim 1 to the mature skin.

6. The method of claim 5, wherein the treatment is an anti-aging treatment.

* * * * *